(12) United States Patent
Omote et al.

(10) Patent No.: US 9,658,174 B2
(45) Date of Patent: May 23, 2017

(54) X-RAY TOPOGRAPHY APPARATUS

(71) Applicant: Rigaku Corporation, Akishima-shi (JP)

(72) Inventors: Kazuhiko Omote, Akiruno (JP);
Keiichi Morikawa, Fuchu (JP);
Yoshinori Ueji, Akishima (JP);
Masahiro Tsuchiya, Tachikawa (JP);
Takeshi Fujimura, Akiruno (JP);
Atsunori Kiku, Hino (JP)

(73) Assignee: RIGAKU CORPORATION,
Akishima-Shi, Tokyo (JP)

( * ) Notice: Subject to any disclaimer, the term of this patent is extended or adjusted under 35 U.S.C. 154(b) by 265 days.

(21) Appl. No.: 14/538,837

(22) Filed: Nov. 12, 2014

(65) Prior Publication Data
US 2015/0146858 A1 May 28, 2015

(30) Foreign Application Priority Data

Nov. 28, 2013 (JP) .................................. 2013-246533

(51) Int. Cl.
*G01N 23/20* (2006.01)
*G01N 23/207* (2006.01)
*G21K 1/06* (2006.01)

(52) U.S. Cl.
CPC ........... *G01N 23/207* (2013.01); *G01N 23/20* (2013.01); *G01N 23/20008* (2013.01);
(Continued)

(58) Field of Classification Search
CPC ............. G01N 23/20; G01N 23/20008; G01N 23/20016; G01N 23/20025; G01N 23/207; G01N 2223/05; G21K 1/062
(Continued)

(56) References Cited

U.S. PATENT DOCUMENTS

| 4,096,389 A * | 6/1978 | Ashe ...................... A61B 6/032 378/147 |
| 5,373,544 A * | 12/1994 | Goebel .................. B82Y 10/00 378/149 |

(Continued)

FOREIGN PATENT DOCUMENTS

| JP | 08-124983 A | 5/1996 |
| JP | 2006-284210 A | 10/2006 |

(Continued)

OTHER PUBLICATIONS http://chelron 2010. Spring 8. Or. Jp /text/bl/11 _BL19B2 .pdf, (file stamp date: Sep. 30, 2010), "beam line BL19B2 at Spring-8, synchrotron radiation facility", 2 pages.

(Continued)

*Primary Examiner* — Allen C. Ho
(74) *Attorney, Agent, or Firm* — Buchanan Ingersoll & Rooney PC

(57) ABSTRACT

Disclosed is an X-ray topography apparatus including an X-ray source, a multilayer film mirror, a slit, a two-dimensional X-ray detector, and a sample moving device that sequentially moves the sample to a plurality of step positions. The X-ray source is a minute focal spot. The multilayer film mirror forms monochromatic, collimated, high-intensity X-rays. The direction in which the multilayer film mirror collimates the X-rays coincides with the width direction of the slit. The step size by which the sample is moved is smaller than the width of the slit. The combination of the size of the minute focal spot, the width of the slit, and the intensity of the X-rays that exit out of the multilayer film mirror allows the contrast of an X-ray image produced when the detector receives X-rays for a predetermined period of 1 minute or shorter to be high enough for observation of the X-ray image.

6 Claims, 15 Drawing Sheets

(52) U.S. Cl.
CPC . *G01N 23/20016* (2013.01); *G01N 23/20025* (2013.01); *G21K 1/062* (2013.01); *G01N 2223/045* (2013.01); *G01N 2223/05* (2013.01); *G01N 2223/315* (2013.01); *G01N 2223/6462* (2013.01); *G21K 2201/064* (2013.01)

(58) Field of Classification Search
USPC ........................................ 378/71–74, 79, 81
See application file for complete search history.

(56) References Cited

U.S. PATENT DOCUMENTS

| | | | | |
|---|---|---|---|---|
| 5,646,976 | A * | 7/1997 | Gutman | B82Y 10/00 378/82 |
| 5,778,039 | A * | 7/1998 | Hossain | G01N 23/20008 378/44 |
| 6,069,934 | A * | 5/2000 | Verman | G01N 23/20016 378/73 |
| 6,226,349 | B1 * | 5/2001 | Schuster | G01N 23/20 378/81 |
| 6,249,566 | B1 * | 6/2001 | Hayashi | G21K 1/06 378/84 |
| 6,307,917 | B1 * | 10/2001 | Shimizu | G21K 1/025 378/145 |
| 6,421,417 | B1 * | 7/2002 | Jiang | B82Y 10/00 359/846 |
| 6,453,006 | B1 * | 9/2002 | Koppel | G01N 23/20 378/70 |
| 6,459,763 | B1 * | 10/2002 | Koinuma | G01N 23/207 378/71 |
| 6,529,578 | B1 * | 3/2003 | Taguchi | G21K 7/00 378/119 |
| 6,577,704 | B1 * | 6/2003 | Holz | G01N 23/2076 378/44 |
| 6,580,940 | B2 * | 6/2003 | Gutman | A61N 5/1001 378/64 |
| 6,624,431 | B1 * | 9/2003 | Foster | B82Y 10/00 250/363.1 |
| 6,744,850 | B2 * | 6/2004 | Fanton | G01N 23/20 378/70 |
| 6,807,251 | B2 * | 10/2004 | Okanda | G01N 23/20 378/71 |
| 6,816,570 | B2 * | 11/2004 | Janik | G01N 23/20 378/50 |
| 6,917,667 | B2 * | 7/2005 | Fujinawa | G21K 1/06 378/70 |
| 7,035,373 | B2 * | 4/2006 | Omote | G21K 1/06 378/71 |
| 7,092,843 | B2 * | 8/2006 | Moore | G01N 23/20 702/179 |
| 7,110,491 | B2 * | 9/2006 | Mazor | G01N 23/20 378/71 |
| 7,116,754 | B2 * | 10/2006 | Lischka | C30B 25/16 378/73 |
| 7,120,228 | B2 * | 10/2006 | Yokhin | G01N 23/20008 378/70 |
| 7,154,992 | B2 * | 12/2006 | Schuster | A61B 6/484 378/79 |
| 7,158,609 | B2 * | 1/2007 | Kikuchi | G01N 23/205 378/70 |
| 7,412,131 | B2 * | 8/2008 | Lee | G21K 1/06 378/21 |
| 7,443,952 | B2 * | 10/2008 | Dosho | G01N 23/20 378/71 |
| 7,646,849 | B2 * | 1/2010 | Iwasaki | B82Y 10/00 378/70 |
| 7,680,246 | B2 * | 3/2010 | Inaba | G01N 23/20 378/71 |
| 7,801,272 | B2 * | 9/2010 | Toraya | G01N 23/207 378/71 |
| 7,920,676 | B2 * | 4/2011 | Yun | G01N 23/201 378/70 |
| 7,983,388 | B2 * | 7/2011 | Michaelsen | G21K 1/04 378/145 |
| 8,208,602 | B2 * | 6/2012 | Lee | B82Y 10/00 378/119 |
| 8,243,878 | B2 * | 8/2012 | Yokhin | G01N 23/207 378/70 |
| 8,311,184 | B2 * | 11/2012 | Lee | A61B 6/032 378/16 |
| 8,340,248 | B2 * | 12/2012 | Toraya | B82Y 10/00 378/70 |
| 8,369,674 | B2 * | 2/2013 | Lee | B82Y 10/00 385/124 |
| 8,437,450 | B2 * | 5/2013 | Wall | G01N 23/207 378/73 |
| 8,687,766 | B2 * | 4/2014 | Wormington | G01N 23/207 378/70 |
| 9,121,812 | B2 * | 9/2015 | Panine | G01N 23/201 |
| 9,269,468 | B2 * | 2/2016 | Ryan | G21K 1/06 |
| 9,335,282 | B2 * | 5/2016 | Omote | G01N 23/207 |
| 2011/0158379 | A1 * | 6/2011 | Cheon | G21K 1/06 378/4 |

FOREIGN PATENT DOCUMENTS

JP    2007-240510 A    9/2007
WO    WO 2008/052287 A1    5/2008

OTHER PUBLICATIONS

"Report on current status of X-ray topography research group" (Spring-8 User's Information/vol. 13 No. 1 Jan. 2008/Research Group Report Spring-8 Users Society//Faculty of Science, University of Toyama, Satoshi Iida, Graduate School of Engineering, Osaka University, Takayoshi Shimura, Japan Synchrotron Radiation Research Institute, Industrial Application Division, Kentaro Kajiwara), 6 pages.

* cited by examiner

FIG. 5
MEASURED DATA
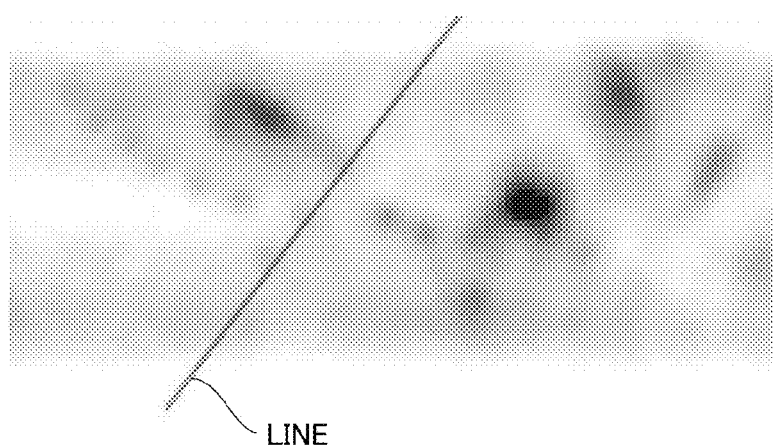
LINE
INTENSITY PROFILE ALONG LINE
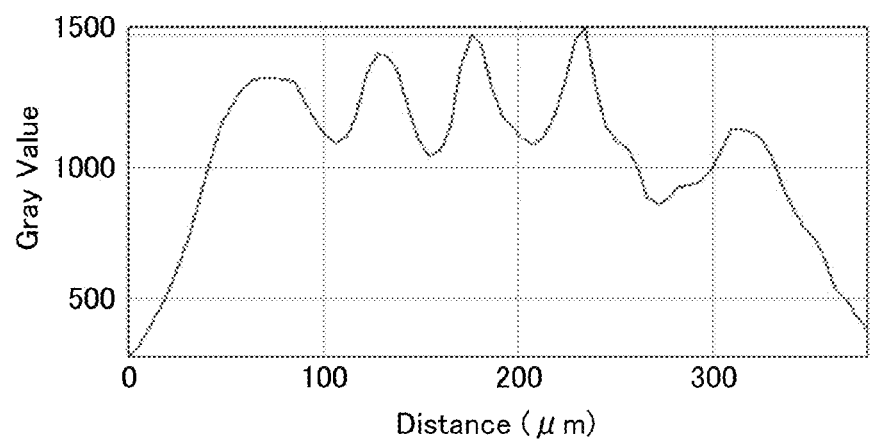

FIG. 6
MEASURED DATA
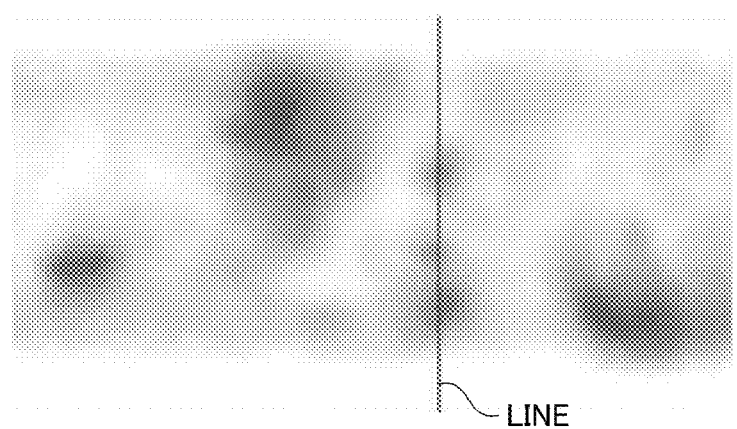
LINE
INTENSITY PROFILE ALONG LINE
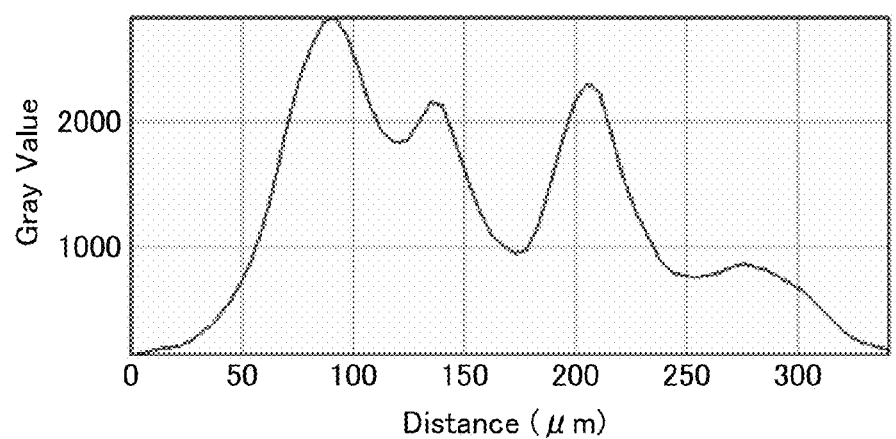

VICINITY OF EPITAXIAL FILM SURFACE

INTERFACE 1 BETWEEN EPITAXIAL FILM AND SUBSTRATE

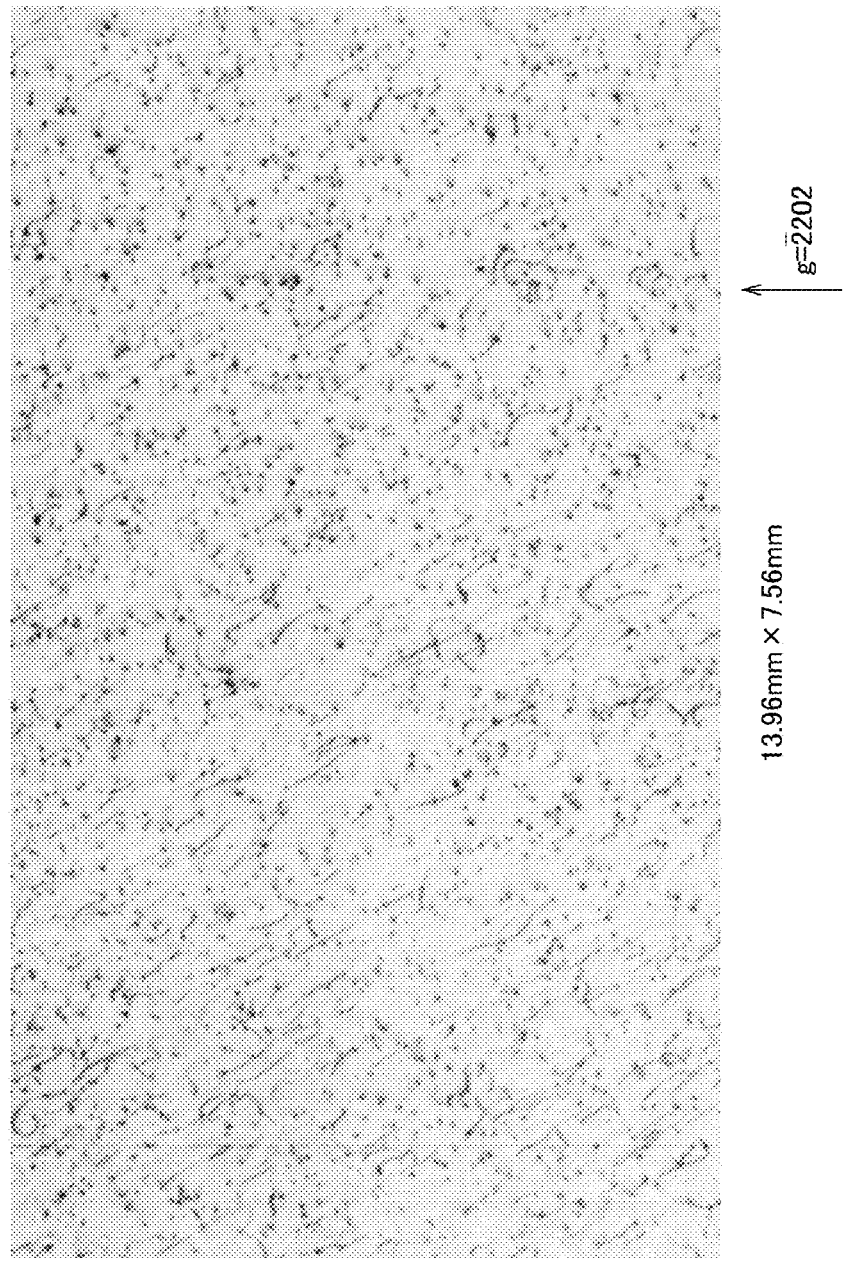

X-RAY TOPOGRAPHY APPARATUS

BACKGROUND OF THE INVENTION

Field of the Invention

The present invention relates to an X-ray topography apparatus that uses X-rays to form a two-dimensional image in correspondence with a crystal defect structure present in a single crystal sample.

Description of the Related Art

There is a known conventional X-ray topography apparatus disclosed, for example, in Patent Citation 1 (Japanese Patent Laid-Open Publication H08-124983). Patent Citation 1 discloses that a single and individual X-ray topographic image is captured. Patent Citation 1, however, does not disclose that a plurality of X-ray topographic images are acquired from a single sample.

Patent Citation 2 (Japanese Patent Laid-Open Publication 2006-284210) describes that a plurality of section topographic images (that is, two-dimensional cross-sectional images) are acquired by using X-rays and then caused to undergo multiple exposure. Patent Citation 2, however, provides no detailed description about the multiple exposure. According to typical interpretation, the multiple exposure is believed to mean exposure of a plurality of images superimposed on a single two-dimensional detector by using a large amount of step movement of the sample.

Patent Citation 3 (WO2008/052287A1) discloses that an X-ray source as small as 10 to 50 μm is used to output X-rays, that the width of the X-rays is limited with a slit, and that a sample is moved stepwise for acquisition of a plurality of diffraction images. Patent Citation 3, however, does not mention the intensity of the X-rays with which the sample is irradiated. When the X-ray source is small and the width of the X-rays is limited with a slit, the intensity of the X-rays that reach the sample is significantly attenuated, which means that the sample needs to undergo very long exposure, for example, for several hours to ten hours in order to provide a single desired X-ray image. No one has therefore considered acquisition of a large number of X-ray images or as many as several hundreds of X-ray images.

Non-Patent Citation 1 (http://cheiron2010.Spring8.or.Jp/text/bl/11_BL19B2.pdf, (file stamp date: 30 Sep. 2010), "beam line BL19B2 at Spring-8, synchrotron radiation facility") discloses that a sample is moved stepwise with respect to synchrotron radiation for acquisition of section topographs of the sample irradiated with the synchrotron radiation in each step position and that the section topographs are superimposed on each other to provide a 3D (three-dimensional) image. Synchrotron radiation, which inherently contains high-intensity X-rays, allows acquisition of a plurality of section topographs in a relatively short period. The period required to acquire a plurality of section topographic images can therefore be greatly shortened. It is, however, impossible to use a synchrotron radiation facility in typical corporate research or manufacturing situations.

Non-Patent Citation 1 does not mention at all use of a laboratory-level X-ray source. Since a laboratory-level X-ray source outputs low-intensity X-rays, acquisition of a plurality of section topographs within a practically acceptable period of time by using the X-ray source is not worth consideration.

Non-Patent Citation 2 is the "Report on current status of X-ray topography research group" (Spring-8 User's Information/Vol. 13 No. 1 Jan. 2008/Research Group Report Spring-8 Users Society//Faculty of Science, University of Toyama, Satoshi IIDA, Graduate School of Engineering, Osaka University, Takayoshi SHIMURA, Japan Synchrotron Radiation Research Institute, Industrial Application Division, Kentaro KAJIWARA). Non-Patent Citation 2 discloses that a sample is scanned with synchrotron radiation and cross-sectional images of several portions of the sample irradiated with the synchrotron radiation are captured, and that the images are superimposed on each other in a computer for estimation of a three-dimensional distribution of in-crystal lattice distortion. Non-Patent Citation 2 does not describe at all use of a laboratory-level X-ray source, too. Since a laboratory-level X-ray source outputs low-intensity X-rays, acquisition of a plurality of section topographic images within a practically acceptable period of time by using the X-ray source is not worth consideration.

Patent Citation 4 (Japanese Patent Laid-Open Publication 2007-240510) discloses an X-ray topography apparatus in which a zone plate or any other X-ray collection means is used to collect X-rays and a sample is irradiated with the collected X-rays. Patent Citation 4 does not mention technologies for outputting X-rays from a minute focal spot, converting X-rays into monochromatic X-rays, collimating X-rays into a collimated beam, or increasing the intensity of X-rays. The apparatus described in Patent Citation 4 cannot therefore acquire a large number of section topographic images in a short period.

SUMMARY OF THE INVENTION

The present invention has been made in view of the problems with the conventional X-ray topography apparatus described above, and an object of the present invention is to acquire a large number of section topographic images or as many as several hundreds of section topographic images by using a laboratory-level X-ray source in a practically acceptable short period, for example, one hour to a dozen of hours.

An X-ray topography apparatus according to the present invention is an X-ray topography apparatus that uses X-rays to form two-dimensional images in correspondence with a crystal defect structure present in a single crystal sample, the apparatus including an X-ray source that produces X-rays with which the sample is irradiated, a multilayer film mirror provided in a position between the sample and the X-ray source, a slit member provided in a position between the sample and the X-ray source and including a slit that limits the width of the X-rays, two-dimensional X-ray detection means for two-dimensionally detecting X-rays having exited out of the sample, and sample moving means for achieving stepwise movement of the sample and the X-rays with which the sample are irradiated relative to each other to sequentially move the sample to a plurality of step positions. The X-ray source produces the X-rays from a minute focal spot. The multilayer film mirror converts the X-rays emitted from the X-ray source into monochromatic, collimated, high-intensity X-rays. The direction in which the multilayer film mirror collimates the X-rays coincides with the width direction of the slit of the slit member. The width of the slit is sufficiently narrower than the thickness of the sample. The step size by which the sample moving means moves the sample is smaller than the width of the slit. The combination of the size of the minute focal spot, the width of the slit, and the intensity of the X-rays that exit out of the multilayer film mirror allows the contrast of an X-ray image produced when the two-dimensional X-ray detection means receives the X-rays for a predetermined period of 1 minute or shorter to be high enough for observation of the X-ray image.

The X-ray topography apparatus allows generation of a large number of two-dimensional cross-sectional images or as many as several-hundred images without a huge X-ray source used in a synchrotron radiation facility but with a laboratory-level X-ray source within a period acceptable in research and manufacturing processes in the industries (within one hour to a dozen of hours, for example). Subsequent observation of the large number of two-dimensional cross-sectional images can provide knowledge of the structure of the sample crystal.

In the configuration described above, even when the X-ray source is a minute focal spot source or the width of the X-rays with which the sample is irradiated is narrowed with the slit, the intensity of the X-rays is high enough to produce an X-ray image having sufficiently high contrast within a predetermined period of one minute or shorter. The intensity of the X-rays described above can be stably achieved by using the multilayer film monochromator.

The reason why the imaging period is limited to one minute or shorter is that an imaging period of one minute or longer requires an impractically very long period for acquisition of several hundreds of two-dimensional cross-sectional images.

In the configuration described above, the X-ray source formed of a minute focal spot, the monochromatic, collimated X-rays, and the narrow slit are requirements for acquisition of high-resolution, clear two-dimensional cross-sectional images. The multilayer film mirror is an element for forming monochromatic, collimated, high-intensity X-rays. Using the multilayer film mirror to increase the intensity of the X-rays allows the X-ray source to be a minute focal spot, and even when the X-rays emitted from the minute focal spot are caused to pass through the narrow slit, the increased intensity X-rays allows an X-ray image having sufficient contrast to be produced within a practically acceptable short predetermined period.

In general, sufficient contrast in the field of X-ray analysis means that a signal (S0) is sufficiently greater than noise (N) in FIG. 4. The noise (N) is typically three times greater than the standard deviation in background. The sufficient signal (S0) is typically at least 1.5 times greater than the noise (N), that is, $$S0 \geq 1.5N.$$

FIGS. 5 and 6 show examples of the contrast of measured data. In the examples shown in FIGS. 5 and 6, contrast high enough for observation is achieved. In both examples, dislocation is clearly extracted. In the images shown in FIGS. 5 and 6, dislocation is expressed with black dots. The profile along each of the lines shown in FIGS. 5 and 6 shows peaks corresponding to the black dots in the image. The S/N ratio changes with peak intensity. Since the noise level is assumed to be about 100, the S/N ratio is about 4 at a low peak in FIG. 5. The S/N ratio is greater than 10 at a high peak in FIG. 6. The period of the measurement made to achieve the results shown in FIGS. 5 and 6 is 60 seconds per image.

Based on X-ray photon statistics, which shows that the S/N ratio is improved by a factor of ½ power of a measurement period of time, even when the measurement period of 60 seconds is shortened by a factor of ¼ to 15 seconds, an S/N ratio of 2 can be theoretically ensured at the low peak in FIG. 5.

The multilayer film monochromator 50 is a monochromator formed by alternately stacking a heavy element layer 51 and a light element layer 52 multiple times on a substrate 53 having a smooth surface, as labelled with reference character 50 in FIG. 2. The heavy element layer 51 and the light element layer 52, each having an appropriate thickness, are alternately and periodically stacked on each other in an appropriate film formation method, for example, a sputtering process. The multilayer film periodic structure provided by repeatedly forming the stacked structure formed of the heavy element layer 51 and the light element layer 52 periodically multiple times allows efficient diffraction of characteristic X-rays, for example, CuKa rays. As a result, high-intensity diffracted X-rays R2 can be produced on the exiting side of the multilayer film monochromator 50.

A surface P1 of the multilayer film monochromator 50 can be formed to be parabolic. The entire parabolic surface P1 allows X-rays R1 incident thereon to be diffracted in parallel to each other. Further, the interplanar spacing of lattice planes in the multilayer film monochromator 50 is so differentiated from each other location-to-location that the X-rays R1 incident at different angles of incidence are reflected off the entire surface P1 of the multilayer film monochromator 50. Specifically, the interplanar spacing of lattice planes on the X-ray incident side, where the angle of incidence is large, are small, whereas the interplanar spacing of lattice planes on the X-ray exiting side, where the angle of incidence is small, are large, with the interplanar spacing of lattice planes in between the two sides continuously changing.

As described above, when the surface P1 of the multilayer film monochromator 50 is a parabolic surface and the interplanar spacing of lattice planes in each position in the parabolic surface is appropriately adjusted, the multilayer film monochromator 50 outputs the high intensity, collimated x-rays. Further, when the total thickness of a pair of the heavy element layer 51 and the light element layer 52, that is, a stacked thickness T2 corresponding to one cycle on the X-ray exiting side is greater than a stacked thickness T1 on the X-ray incident side, the intensity of the X-rays R2 outputted from the multilayer film monochromator 50 and applied through the slit to the sample can be higher than the intensity of the X-rays in a case where no multilayer film monochromator 50 mirror is used.

Conceivable examples of the heavy element may include W (tungsten), Mo (molybdenum), and Ni (nickel). Conceivable examples of the light element may include Si (silicon), C (carbon), and $B_4C$. Conceivable examples of the stacked structure may include a two-layer structure using two types of element and a multilayer structure using at least three types of element. Further, the number of stacked heavy element layer 51 and light element layer 52 can, for example, be about 200. Moreover, the one-cycle thickness of the layer formed of a single heavy element layer 51 and a single light element layer 52 can be set at a value ranging, for example, from 20 to 120 angstroms.

In the X-ray topography apparatus according to the present invention, irradiating the sample with the X-rays in each of the plurality of step positions for the predetermined period and detecting X-rays having exited out of the sample irradiated with the X-rays with the two-dimensional X-ray detection means allow acquisition of a two-dimensional cross-sectional image associated with each of the step positions, formation of a three-dimensional image by arranging the plurality of two-dimensional cross-sectional images, and acquisition of a second two-dimensional image by extracting data along a flat plane different from the measurement planes associated with the three-dimensional image.

In the X-ray topography apparatus according to the present invention, dislocation density can be calculated based on the second two-dimensional image.

In the X-ray topography apparatus according to the present invention, the minute focal spot can be a focal spot so sized that it falls within a circle having a diameter of 100 µm, and the width of the slit can be set at a value ranging from 10 to 50 µm.

EFFECTS OF THE INVENTION

The X-ray topography apparatus according to the present invention allows generation of a large number of two-dimensional cross-sectional images or as many as several hundreds of two-dimensional cross-sectional images without a huge X-ray source used in a synchrotron radiation facility but with a laboratory-level X-ray source within a period acceptable in research and manufacturing processes in the industries (within one hour to a dozen of hours, for example). Subsequent observation of the large number of two-dimensional cross-sectional images allows knowledge of a crystal defect structure in the sample.

BRIEF DESCRIPTION OF THE DRAWINGS

FIG. 5 shows an X-ray image and a diffracted X-ray profile corresponding to the image in an exemplary case where good contrast is achieved;

FIG. 6 shows an X-ray image and a diffracted X-ray profile corresponding to the image in another exemplary case where good contrast is achieved;

FIG. 15 shows a second two-dimensional image of a plane on the rear side of the substrate provided in an experiment.

DESCRIPTION OF THE PREFERRED EMBODIMENTS

Figure 1:
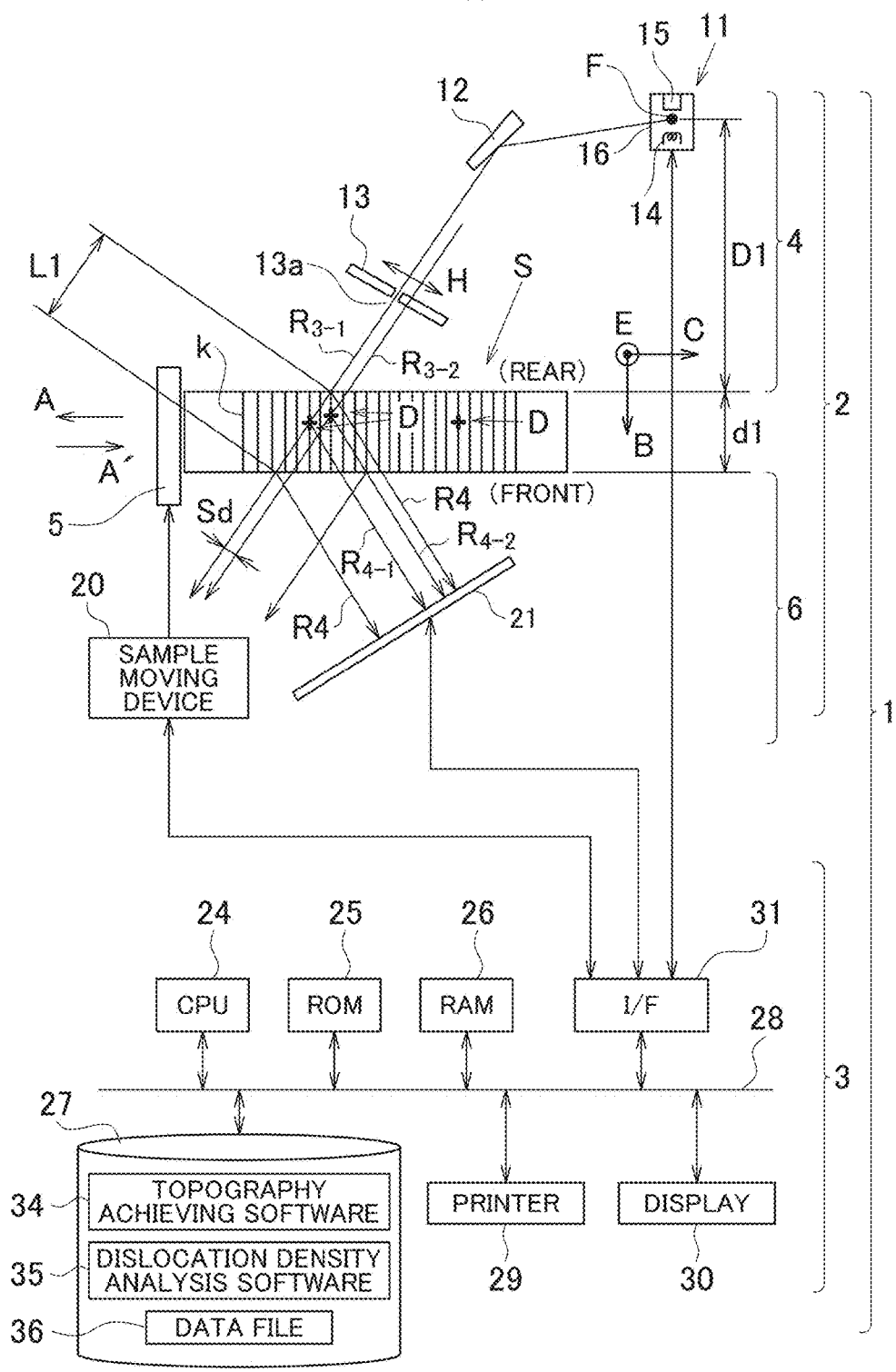
FIG. 1 shows an embodiment of an X-ray topography apparatus according to the present invention.

An X-ray topography apparatus according to the present invention will be described below based on an embodiment. The present invention is not, of course, limited to the embodiment. In the drawings accompanying the present specifications, each component is drawn in some cases in a ratio different from an actual ratio for ease of illustration of a characteristic portion of the component.

FIG. 1 shows an embodiment of the X-ray topography apparatus 1 according to the present invention. An X-ray topography apparatus 1 shown in FIG. 1 includes a measurement system 2 and a control system 3. The measurement system 2 includes an incident optical system 4, a sample stage 5, and a reception optical system 6.

(Incident Optical System)

The incident optical system 4 includes an X-ray tube 11, a multilayer film mirror 12, and a slit member 13. The X-ray tube 11 has a filament 14, which is a cathode, and a target 15, which is an anode. When the filament 14 is energized (that is, when current is caused to flow through filament 14), electrons are discharged from the filament 14. An area of the surface of the target 15 on which the discharged electrons are incident is an X-ray focal spot F. Xrays are radiated from the X-ray focal spot F. The X-ray focal spot F functions as an X-ray source. The radiated X-rays are extracted as point-focused X-rays through an X-ray window 16. The X-ray focal spot F of the thus extracted X-rays is a minute focal spot having a size that falls within a circle having a diameter of 100 µm. A distance D1 from the X-ray focal spot F to a sample S is 800 mm.

Figure 2:
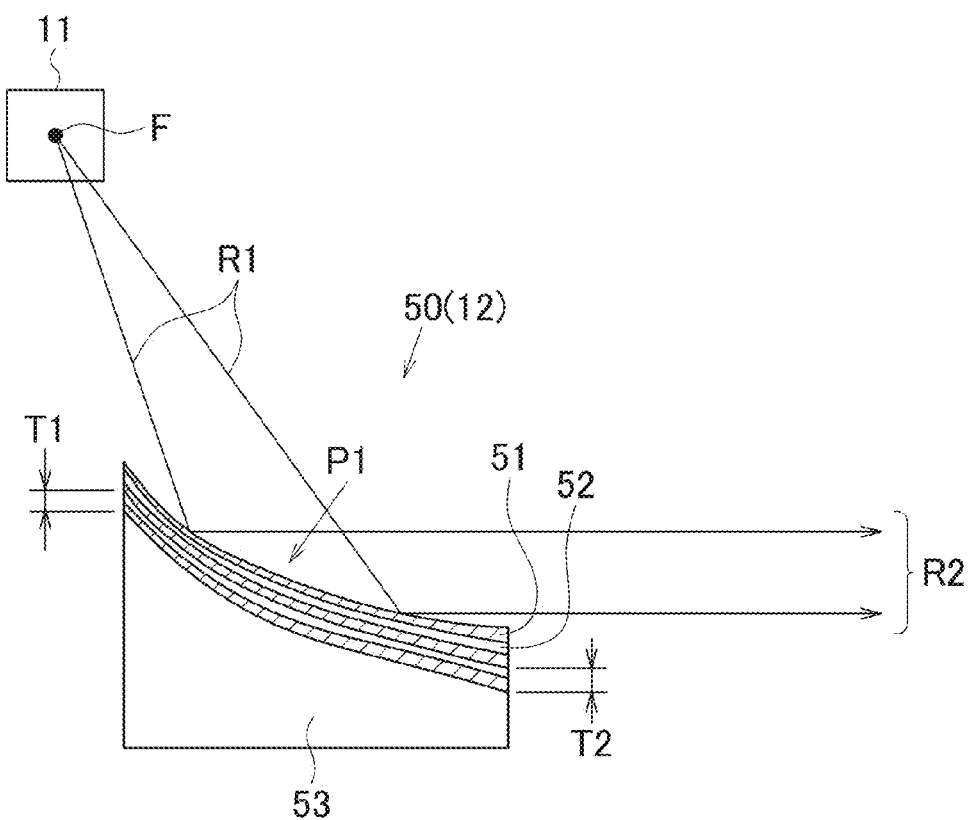
FIG. 2 is a cross-sectional view showing an example of a multilayer film mirror that is a key part of the X-ray topography apparatus shown in FIG. 1.

The multilayer film mirror 12 is formed of the multilayer film monochromator 50 shown in FIG. 2. The multilayer film mirror 12 converts the X-rays emitted from the X-ray tube 11 into monochromatic, collimated, higher-intensity X-rays. The collimation is performed in the direction along a width direction H of a slit 13a of the slit member 13. The monochromatic, collimated, higher-intensity X-rays produced by the multilayer film mirror 12 allow generation of a large number of segment topographic images (that is, partial two-dimensional cross-sectional images) or as many as 400 images within a short period, as will be described later.

The width of the slit 13a is a predetermined width ranging, for example, from 10 to 50 µm. A width of the slit 13a smaller than 10 µm attenuates the intensity of the X-rays so much that clear segment topographic images may not be produced. On the other hand, a width of the slit 13a greater than 50 µm may not produce sharp (that is, clear) segment topographic images.

(Sample Stage)

The sample crystal (hereinafter also simply referred to as sample) S, which is an object under measurement, is placed on the sample stage 5. The sample stage 5 is not drawn in accordance with an actual shape but is diagrammatically drawn. The thickness d1 of the sample S ranges, for example, from 0.2 to 2 mm. The sample S extends in the direction passing through the plane of view of FIG. 1. Each of a plurality of crystal lattice planes k present in the sample S extends roughly along the direction of the thickness d1 of the sample S. Further, the crystal lattice planes k are arranged at equal intervals in parallel to each other along a direction roughly perpendicular to the direction of the thickness d1 of the sample S.

The sample stage 5 is provided with a sample moving device 20. The sample moving device 20 can linearly move the sample stage 5 intermittently or stepwise in the direction indicated by the arrow A. The sample moving device 20 can further linearly move the sample stage 5 in a returning direction indicated by the arrow A'. The directions A-A' are parallel to the surface of the sample S. The sample moving device 20 is formed of an arbitrary linearly driving mechanism. The linearly driving mechanism can be formed, for example, of a mechanism using a feed screw shaft driven by a pulse motor or any other power source. A pulse motor is a motor capable of controlling the angle of rotation of an output shaft thereof.

X-rays R3-1 having passed through the slit 13a of the slit member 13 penetrates the sample S in the width direction (direction of the thickness d1 of the sample S) thereof. When the sample stage 5 moves in the direction A by a predetermined step width and the sample S moves in the direction A by the same step width accordingly, X-rays R3-2 are incident on the next step position on the sample S. Thereafter, whenever the sample S moves by the fixed step width, subsequent X-rays are incident on the respective step positions on the sample S.

A step width Sd of the step movement (that is, intermittent movement) of the sample S is smaller than the width of the slit 13a of the slit member 13. As a result, among a plurality of section topographic images (that is, two-dimensional cross-sectional images) formed by the X-rays R3-1, X-rays R3-2, etc., adjacent section topographic images are not separated with a gap therebetween but can be seamlessly connected to each other.

(Reception Optical System)

The reception optical system 6 includes a two-dimensional X-ray detector 21. The two-dimensional X-ray detector 21 extends in the direction passing through the plane of view of FIG. 1 and receives the X-rays having exited out of the sample S, that is, diffracted X-rays R4 in a planar manner, that is, in a two-dimensional manner. The two-dimensional X-ray detector 21 can, for example, be formed of a photon-counting-type pixel two-dimensional X-ray detector (that is, pulse-counting-type pixel array two-dimensional detector) or a two-dimensional CCD and/or CMOS detector.

The photon-counting-type pixel two-dimensional X-ray detector is an X-ray detector having a plurality of two-dimensionally arranged pixels each of which directly converts a photon into an electric signal. The two-dimensional detector is an X-ray detector having a plurality of charge coupled device (CCD) elements arranged in a planar manner.

(Control System)

The control system 3 is formed of a computer in the present embodiment. Specifically, the control system 3 includes a CPU 24, a read only memory (ROM) 25, a random access memory (RAM) 26, a memory 27, and a bus 28, which connects the components described above to each other. The memory 27 is formed, for example, of a hard disk drive or any other mechanical memory or a semiconductor memory. A printer 29, which is an example of image display means, and a display 30, which is another example of the image display means, are connected to the bus 28.

The X-ray tube 11, the two-dimensional X-ray detector 21, and the sample moving device 20, which are components of the measurement system 2, are connected to the bus 28 via an interface 31. In the memory 27 are installed topography achieving software 34, which is function achieving means for driving the measurement system 2 to achieve desired topographic measurement, and dislocation density analysis software 35, which is software for analyzing measured data. Further, in the memory 27 is provided a data file 36, which is an area where measured data and analyzed data are stored.

(Operation)

The operation of the X-ray topography apparatus 1 shown in FIG. 1 will next be described with reference to the flowchart shown in FIG. 3. First, in step S1, initial adjustment is made to locate each element in FIG. 1 in a predetermined initial position. Measurement is then initiated in a case where an operator has instructed initiation of the measurement (YES in step S2).

Specifically, in step S3, the X-ray tube 11 in FIG. 1 is operated to radiate X-rays. The radiated X-rays are converted by the multilayer film mirror 12 into monochromatic, collimated, higher-intensity X-rays. The X-rays having undergone the processes carried out by the multilayer film mirror 12 are then narrowed in terms of width by the slit 13a of the slit member 13 and incident on the sample S. Reference character R3-1 denotes the incident X-rays in FIG. 1. The X-ray irradiation continues for a predetermined period, for example, one minute or shorter. At this point, when a diffraction condition is satisfied between the incident X-rays R3-1 and the crystal lattice planes k, the diffracted X-rays R4 are produced. The X-rays R4 are detected with the two-dimensional X-ray detector 21 (step S4).

Figure 7:
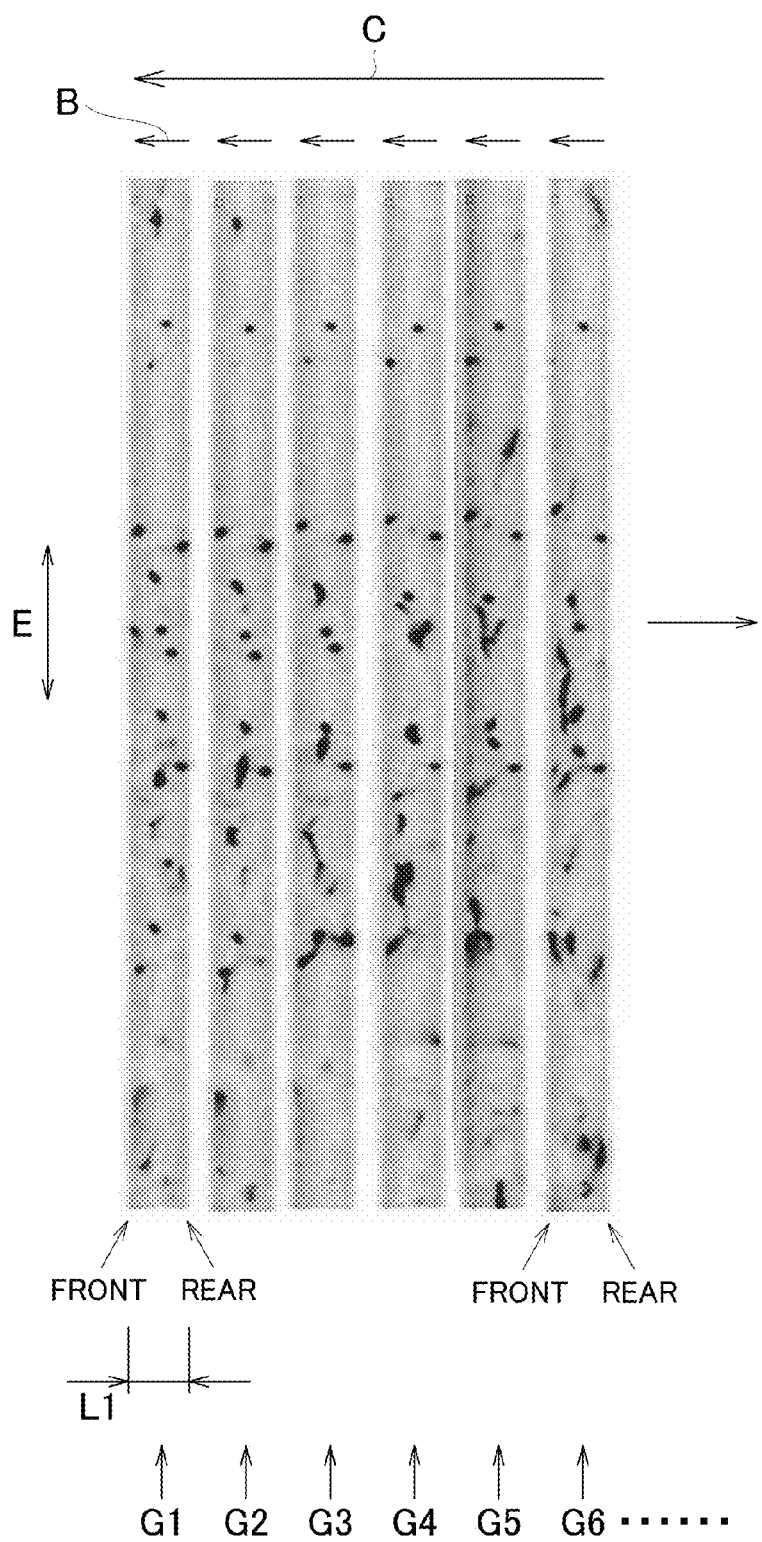
FIG. 7 shows an example of two-dimensional cross-sectional images (that is, section topographic images) produced by the X-ray topography apparatus in FIG. 1.

FIG. 7 shows an example of two-dimensional cross-sectional images (what is called section topographic images) detected with the two-dimensional X-ray detector 21 in FIG. 1. In FIG. 7, an elongated rectangular image labelled with reference character G1 represents a two-dimensional cross-sectional images produced by the incident X-rays R3-1 in FIG. 1. When a lattice defect D is present in a path along which the incident X-rays R3-1 travels in FIG. 1, high-intensity diffracted X-rays R4-1 corresponding to the defect are produced in the portion where the defect is present, and the high-intensity diffracted X-rays produce a black dot in the two-dimensional cross-sectional image G1. That is, it is shown that a lattice defect is present in a position in the sample S that corresponds to the position where the black dot is formed in the two-dimensional cross-sectional image G1.

In FIG. 7, the direction indicated by the arrows B corresponds to the direction in which the X-rays R3-1 in FIG. 1 travel (that is, thickness direction of sample S). The width L1 of the two-dimensional cross-sectional image G1 in FIG. 7 corresponds to the path along which the incident X-rays R3-1 pass through the sample S in FIG. 1. The direction indicated by the arrow C in FIG. 7 corresponds to the scan direction C in FIG. 1. The direction labelled with reference character E in FIG. 7 is the direction passing through the plane of view of FIG. 1 (that is, direction perpendicular to scan direction C along which sample S is scanned).

The predetermined period described above for which the sample S is irradiated with the incident X-rays R3-1 is a period that allows sufficient contrast, that is, a sufficient S/N ratio between the background and the black dots in the two-dimensional cross-sectional image G1 produced by the two-dimensional X-ray detector 21. In the present embodiment, since the multilayer film mirror 12 is provided in the X-ray optical path in the incident optical system 4 to increase the intensity of the X-rays, the X-ray irradiation period can be significantly shortened as compared with a conventional apparatus using no multilayer film mirror. Specifically, it takes several tens of minutes for a conventional X-ray topography apparatus to produce the single two-dimensional cross-sectional image G1, whereas in the present embodiment, the characteristics of the X-ray source 11 and the multilayer film mirror 12 are so optimized that sufficient contrast is achieved in a predetermined period of one minute or shorter, preferably 10 to 20 seconds, more preferably 10 seconds.

After the predetermined period for X-ray exposure has elapsed as described above (YES in step S5 in FIG. 3), the CPU 24 (FIG. 1) extracts an X-ray intensity signal from the two-dimensional X-ray detector 21 (step S6 in FIG. 3), data carried by the signal (that is, data corresponding to two-dimensional cross-sectional image G1 in FIG. 7) is stored in the data file 36 in the memory 27 (step S7 in FIG. 3).

Figure 3:
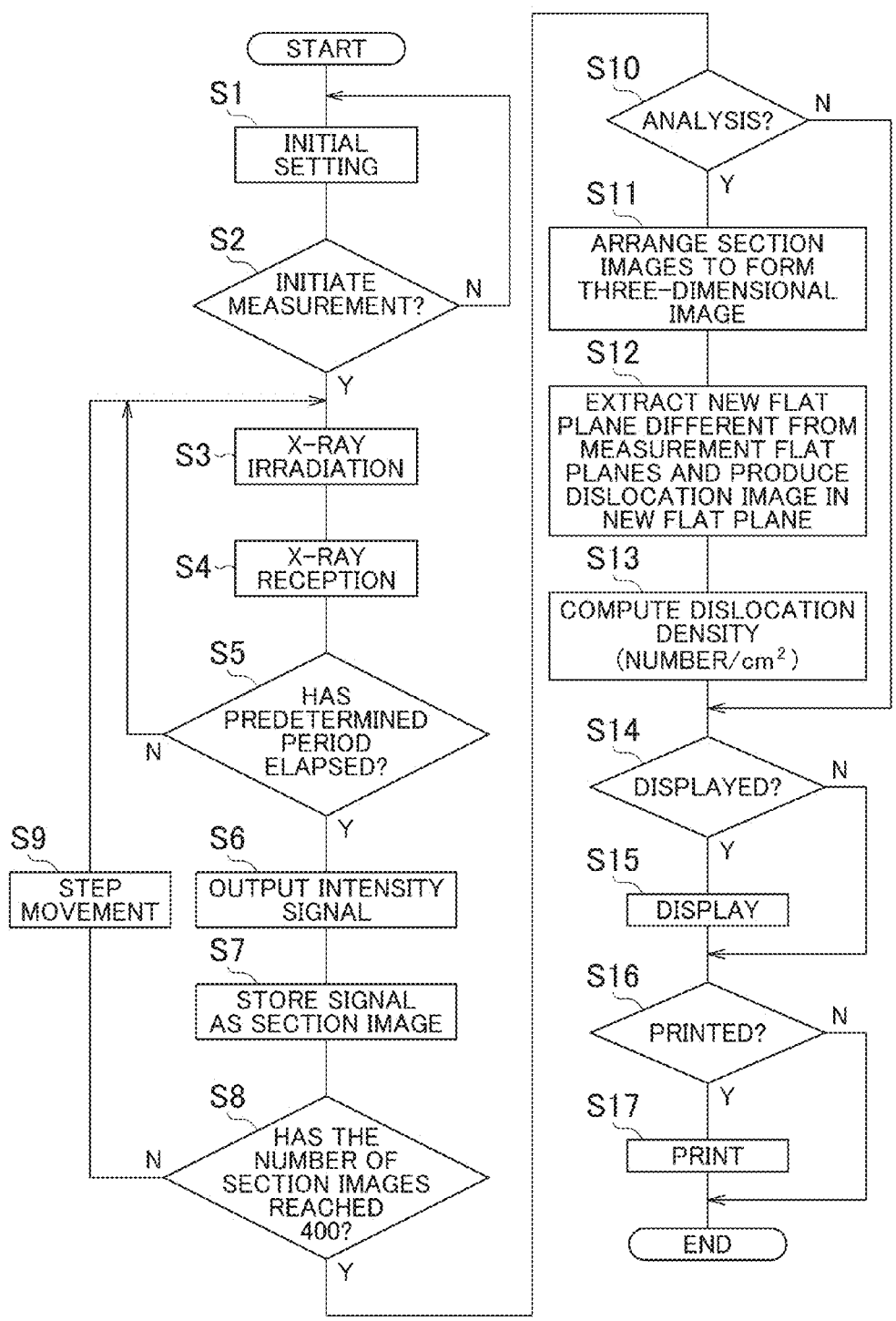
FIG. 3 is a flowchart showing the procedure of operation performed by the X-ray topography apparatus in FIG. 1.
Figure 4:
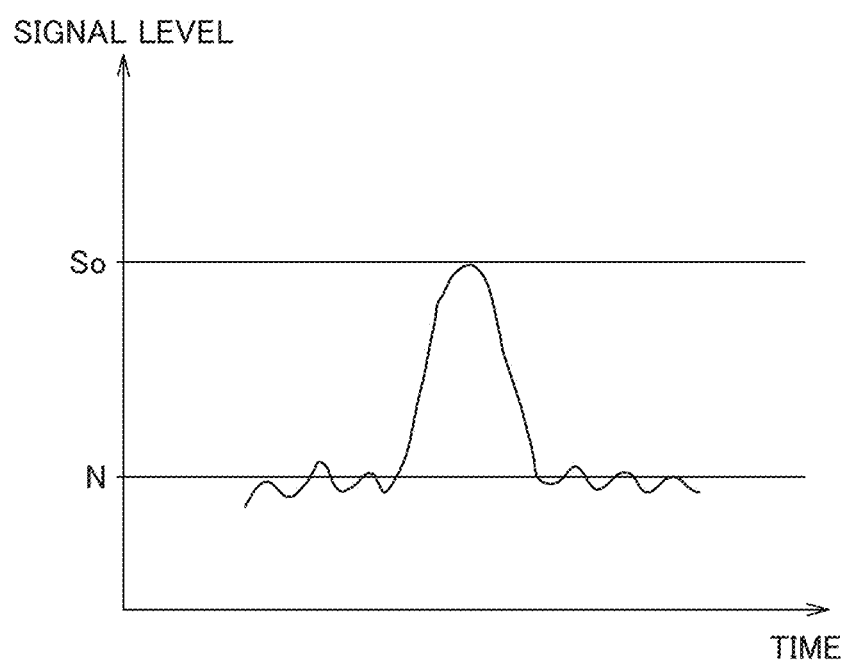
FIG. 4 is a graph showing the contrast between a dislocation image and background in an X-ray image.

When imaging using the incident X-rays R3-1 in a single position on the sample S is completed, the CPU 24 instructs the sample moving device 20 to move the sample stage 5 and hence the sample S by the predetermined step width Sd in the direction indicated by the arrow A and stop the sample stage 5 and hence the sample S in the post-movement position (NO in step S8, step 9 in FIG. 3). The step width Sd is, for example, 10 µm. The step width Sd is set to a value smaller than the width of the slit 13a of the slit member 13.

As a result, a state in which the incident X-rays R3-2 are incident on an adjacent step position separated by the step width Sd is achieved. In this state, steps S3 to S7 in FIG. 3 are repeated, and a two-dimensional cross-sectional image G2 in FIG. 7 is produced in the form of data in the X-ray intensity signal and stored. When a lattice defect D is present in the path along which the incident X-rays R3-2 travel, high-intensity diffracted X-rays R4-2 corresponding to the defect are produced, and the diffracted X-rays produce a black dot in the two-dimensional cross-sectional image G2.

Thereafter, the step movement of the sample S and the X-ray measurement are repeatedly performed until a predetermined large number of two-dimensional cross-sectional images G1, G2, ... Gn, for example, 400 two-dimensional cross-sectional images are produced (NO in step S8, step S9 in FIG. 3). As a result, a large number of two-dimensional cross-sectional images G1, G2, ... Gn associated with the step positions on the sample S are stored, as shown in FIG. 7.

Figure 8:
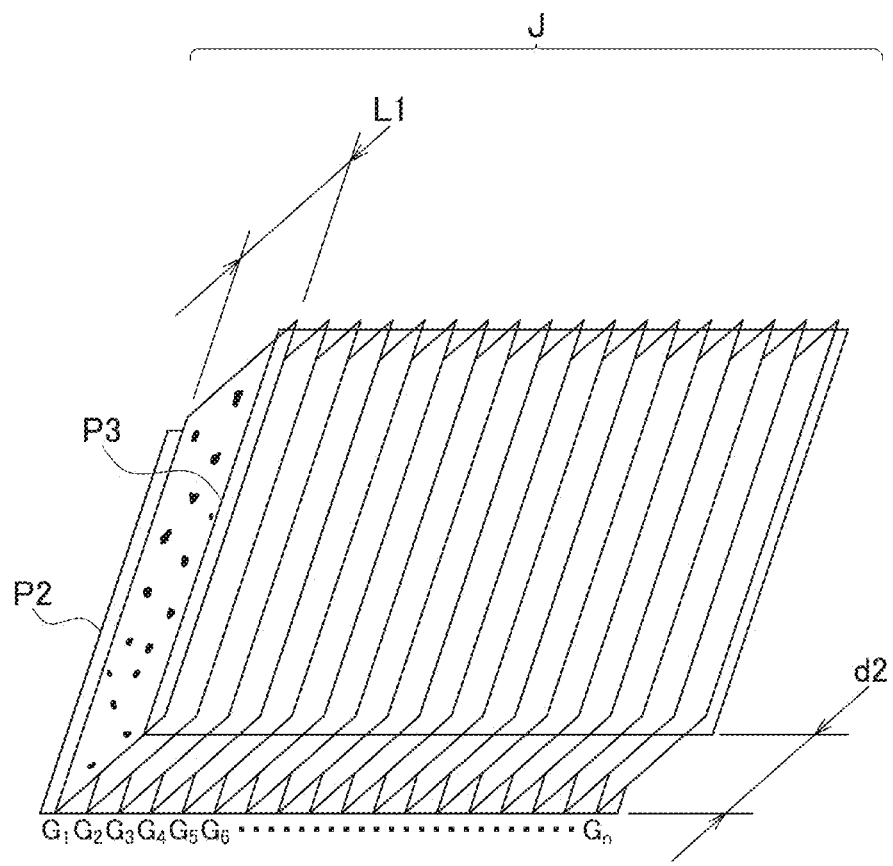
FIG. 8 shows an example of a three-dimensional image produced by the X-ray topography apparatus in FIG. 1.

After the measurement is made for the predetermined number of images (YES in step S8), and when an operator instructs analysis (YES in step S10), the CPU 24 produces, in step S11 in FIG. 3, a three-dimensional image J diagrammatically shown in FIG. 8 and stores the three-dimensional image J in the memory. The three-dimensional image J is formed by arranging the large number of (400 in the present embodiment) two-dimensional cross-sectional images G1, G2, G3, ... Gn associated with the respective step positions on the sample S in such a way that the images are superimposed on each other in a three-dimensional coordinate system Z. The three-dimensional coordinate system Z has a horizontal axis representing a movement distance X, a vertical axis representing a direction E perpendicular to the sample scan direction, and a height axis representing the direction in which the X-rays travel (or direction of sample thickness d1).

The CPU 24 then produces a second two-dimensional image in step S12 and stores them in the memory. Specifically, the three-dimensional image J is sectioned along a flat plane different from the plane where the measurement was made, and data on dislocation images (i.e., black dots) in the flat plane are gathered and stored in the memory. For example, in FIG. 8, data that belong to a surface P2 of the three-dimensional image J are gathered and stored, and data that belong to a flat plane P3 separated from the surface by a distance d2 are gathered and stored.

Figure 9:
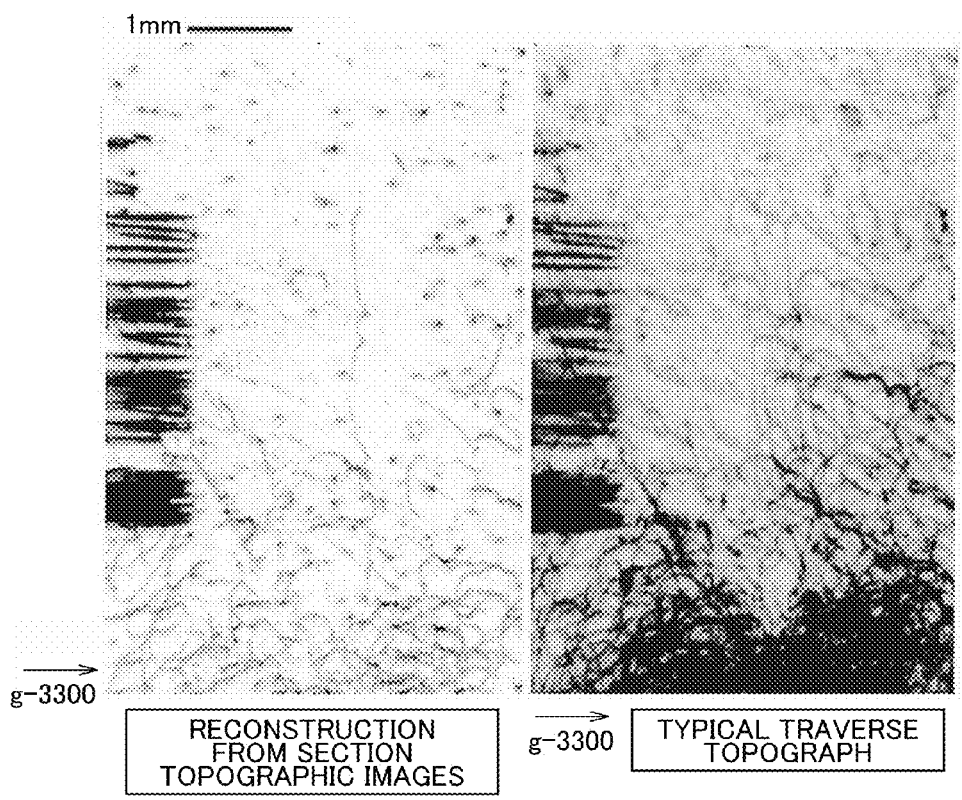
FIG. 9 shows an example of a second two-dimensional image produced by the X-ray topography apparatus in FIG. 1 (left hand side) and conventional transmission topography image (right hand side)

The resulting second two-dimensional image is displayed, for example, in the form of the left photograph in FIG. 9. The photograph is a displayed image formed by measuring an SiC wafer as the sample S in FIG. 1 to produce a three-dimensional image J, such as that shown in FIG. 8, and gathering dislocation data in the surface P2 or a surface in the vicinity thereof. The measurement conditions were as follows:

Step movement intervals: 10 µm
The number of acquired two-dimensional cross-sectional images (section topographic images): 400
Measurement period spent to acquire single two-dimensional cross-sectional image: 50 seconds
Field of view: 4 mm×6 mm In the photograph, the long lines show that dislocation extends in the flat plane, and the dots show that the dislocation extends in the thickness direction of the sample.

The right photograph in FIG. 9 is presented for comparison purposes and is a two-dimensional image produced by measuring the same place of the sample using a traverse transmission topography technique, which is a conventional topography measurement technique. In the traverse topography technique, in which data in cross sections are integrated in a two-dimensional X-ray detector, all dislocation sites present in the sample are superimposed on each other, and the operator views the superimposed image. Dislocation information at a certain depth in the sample cannot therefore be accurately reflected in the image. In contrast, in the present embodiment a result of which is shown in the left portion of FIG. 9, dislocation information in the flat plane at the certain depth is accurately reflected. It is therefore clearly shown that the present embodiment allows accurate discrimination between and identification of basal plane dislocation, threading screw dislocation, and threading edge dislocation.

The CPU next calculates dislocation density in step S13 in FIG. 3. That is, dislocation density (number of dislocation sites/cm$^2$) is calculated based on dislocation images in the flat plane that are produced in the form of the left photograph in FIG. 9. Thereafter, image display using the display 30 is performed as required (steps S14, S15), and image printing using the printer 29 is further performed as required (steps S16, S17).

As described above, the present embodiment allows measurement of a high-contrast image of dislocation present in a cross section along an incident X-ray beam. A large number of X-ray measurement are made while a cross section irradiated with X-rays is slightly shifted whenever single X-ray measurement is made for acquisition of a large number of section topographic images, and analysis of the section topographic images provides a three-dimensional structure of dislocation in a wafer. Cutting the resultant three-dimensional image in a direction parallel to the surface of the sample provides an image of dislocation present in a plane at a fixed depth.

The present embodiment allows observation of dislocation present in a position in the vicinity of a surface and observation of only dislocation present at a fixed depth from the surface. Comparison of the present embodiment with reflective X-ray topography measurement using synchrotron radiation has proved that threading edge dislocation is observable.

Further, the present embodiment can provide clear knowledge of the path along which dislocation extends. For example, it can be determined whether dislocation is parallel to a surface, extends from rear to front, or extend from front to rear and is redirected back toward the front.

It can further be evaluated that the surface of a sample has many dots representing threading dislocation or the interior of the sample has may lines representing basal plane dislocation.

Other Embodiments

The present invention has been described with reference the preferable embodiment, but the invention is not limited thereto and a variety of changes can be made thereto within the scope of the invention set forth in the claims.

For example, the multilayer film mirror 12 in FIG. 1 is not limited to a multilayer film mirror shaped as shown in FIG. 2 and can be arbitrarily shaped as required. Further, the control procedure shown in FIG. 3 is an example and can be modified as required.

EXAMPLES

Figure 10:
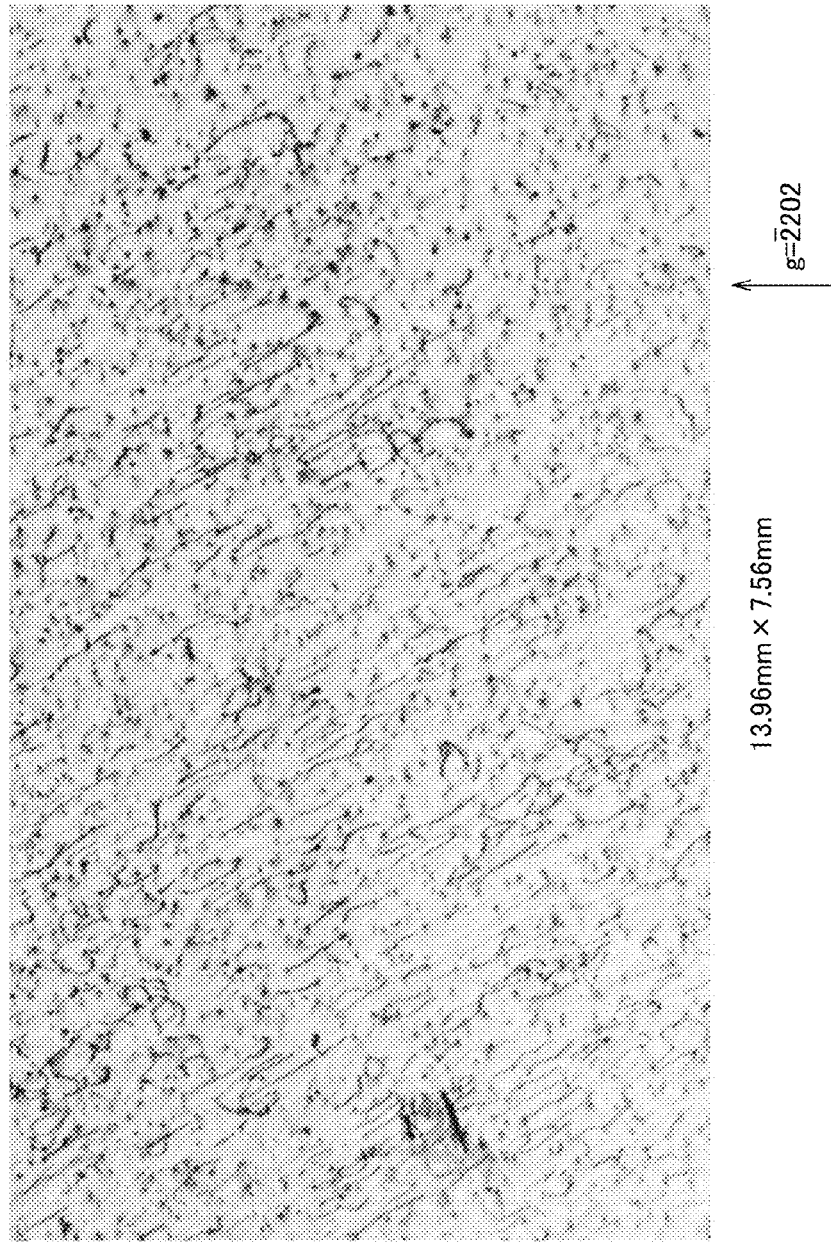
FIG. 10 shows a second two-dimensional image of a plane in the vicinity of the surface of an epitaxial film provided in an experiment.
Figure 11:
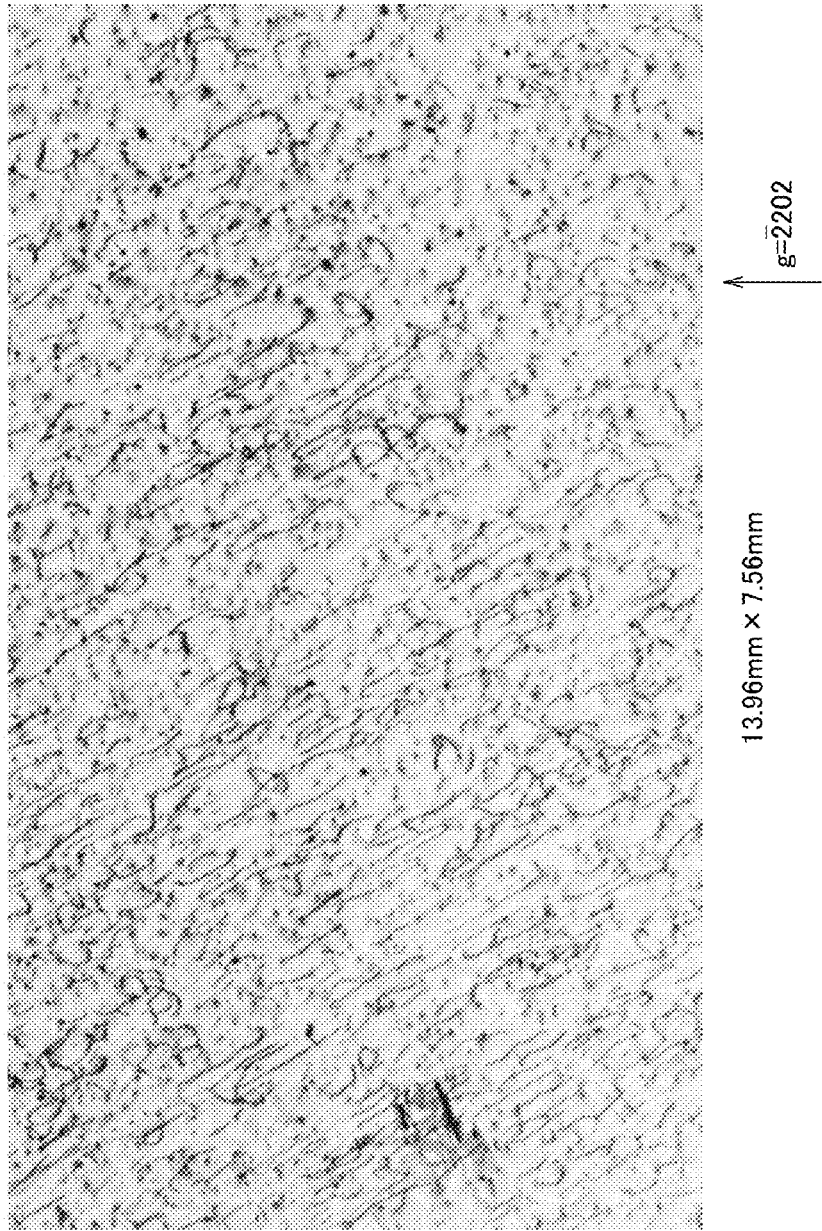
FIG. 11 shows a second two-dimensional image of a plane at a location in the interface between the epitaxial film and a substrate provided in an experiment.
Figure 12:
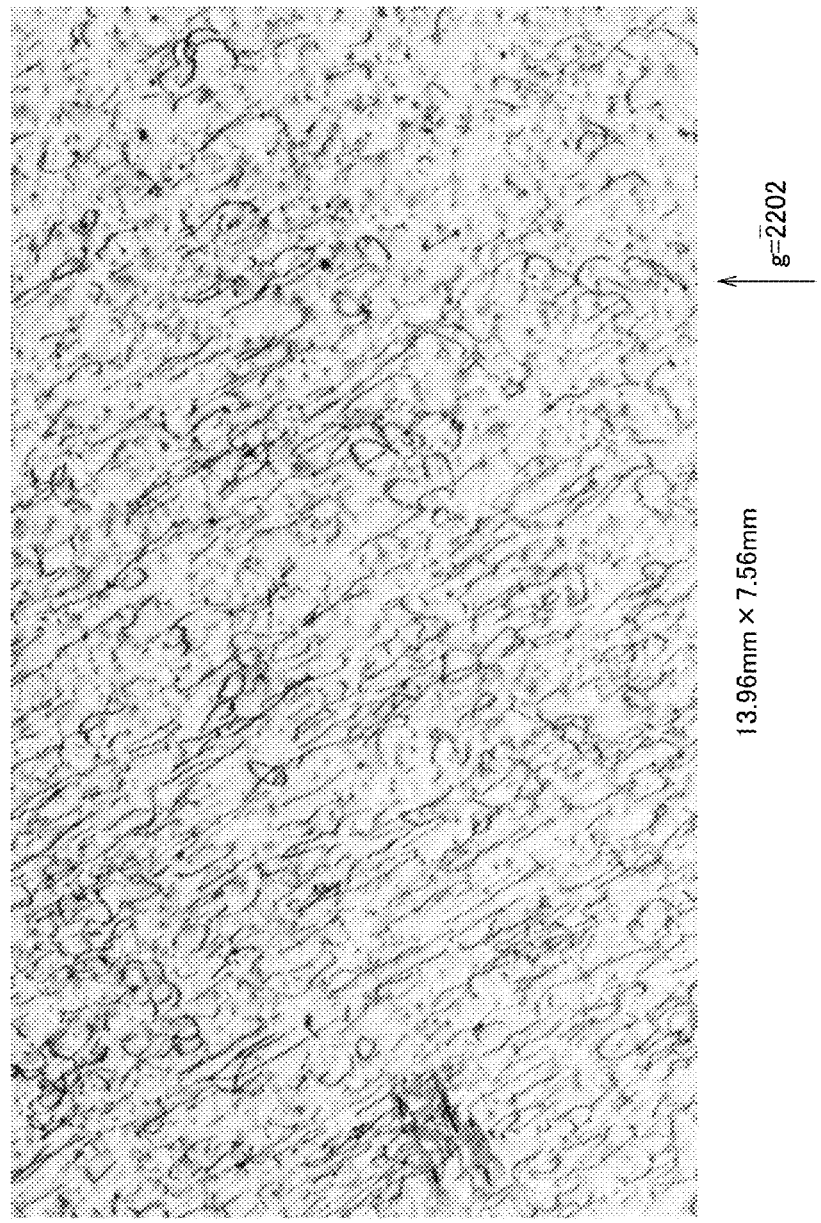
FIG. 12 shows a second two-dimensional image of a plane at another location in the interface between the epitaxial film and the substrate provided in an experiment.
Figure 13:
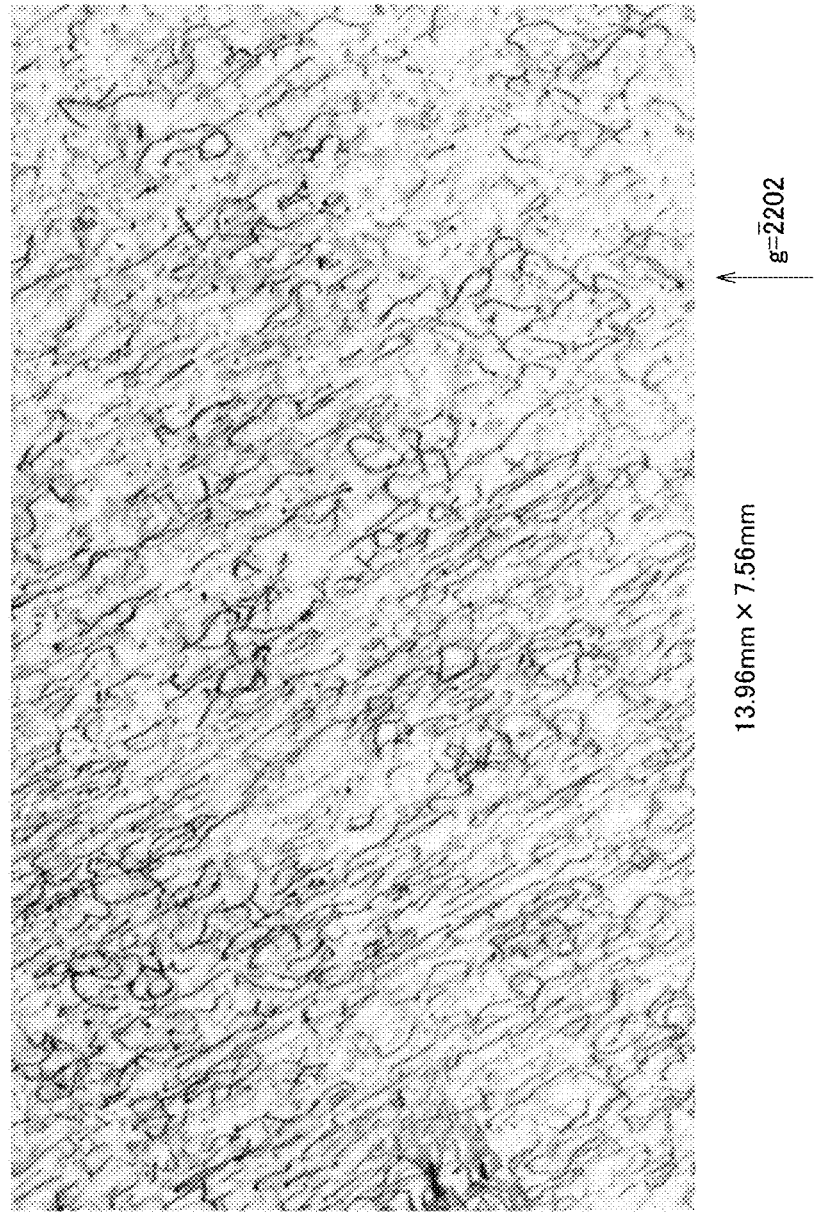
FIG. 13 shows a second two-dimensional image of a plane at a location in the substrate provided in an experiment.
Figure 14:
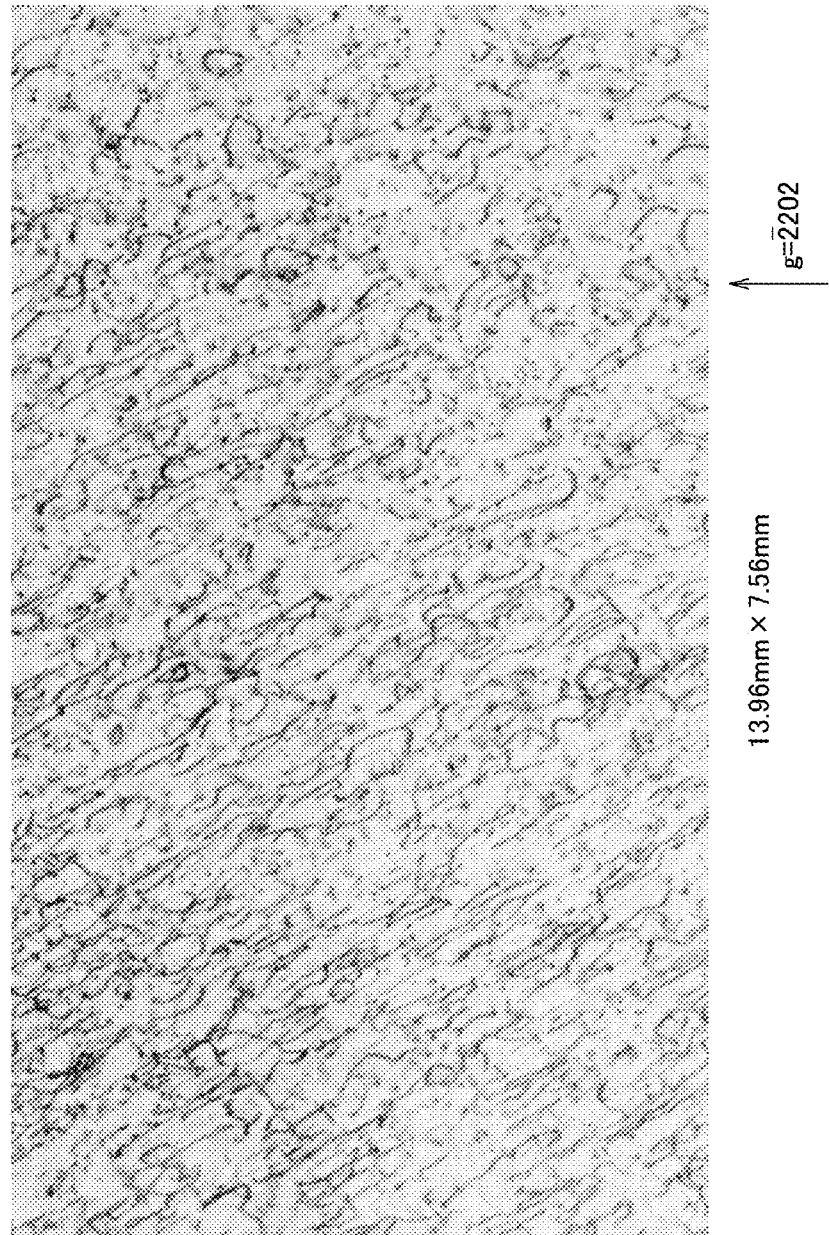
FIG. 14 shows a second two-dimensional image of a plane at another location in the substrate provided in an experiment.

A crystal formed by growing an SiC epitaxial film on an SiC substrate to a thickness of about 10 μm, that is, a homoepitaxial crystal, which is grown under the condition that the substrate and the film are made of the same crystal, was measured as a sample by using the X-ray topography apparatus in FIG. 1. As a result, a second two-dimensional image of a plane in the vicinity of the surface of the epitaxial film was produced as shown in FIG. 10. Further, a second two-dimensional image of a plane at an interface between the epitaxial film and the substrate was produced as shown in FIG. 11. Moreover, a second two-dimensional image of a plane at another interface between the epitaxial film and the substrate was produced as shown in FIG. 12. Further, a second two-dimensional image of a plane at a location in the substrate was produced as shown in FIG. 13. Moreover, a second two-dimensional image of a plane at another location in the substrate was produced as shown in FIG. 14. Further, a second two-dimensional image of a plane on rear side of the substrate was produced as shown in FIG. 15.

EXPLANATION OF SYMBOLS

1. X-ray topography apparatus, 2. Measurement system, 3. Control system, 4. Incident optical system, 5. Sample stage, 6. Reception optical system, 11. X-ray tube, 12. Multilayer film mirror, 13. Slit member, 13a. Slit, 14. Filament (cathode), 15. Target (anode), 16. X-ray window, 20. Sample moving device, 21. Two-dimensional X-ray detector, 27. Memory, 28. Bus, 29. Printer (image display means), 30. Display (image display means), 31. Interface, 34. Topography achieving software, 35. Dislocation density analysis software, 36. Data file, 50. Multilayer film monochromator, 51. Heavy element layer, 52. Light element layer, 53. Substrate, B. Direction along thickness of sample, C. Direction in which sample is scanned by X-rays, D. Lattice defect, D1. Distance from X-ray focal spot to sample, d1. Thickness of sample, d2. Separated planes distance, E. Direction perpendicular to scanning direction, F. X-ray focal spot (X-ray source), G1, G2, G3, . . . Gn. Two-dimensional cross-sectional image, H. Direction of slit width, J. Three-dimensional image, k. Crystal lattice planes, L1. Width of two-dimensional cross-sectional images, P1. Surface, P2,P3. Planes for sectioning three-dimensional image, R1: Incident X-rays, R2: Diffracted X-rays, R3-1,R3-2: Incident X-rays, R4-1,R4-2: Diffracted X-rays, S: Sample crystal, Sd: Step width, T1: Stacked layer thickness on X-ray incident side, T2: Stacked layer thickness on X-ray exiting side, X: Horizontal axis representing sample moving distance, Z: Three-dimensional coordinate system,

The invention claimed is:

1. An X-ray topography apparatus that uses X-rays for form two-dimensional images in correspondence with an internal structure of a sample, comprising:
  an X-ray source that produces X-rays with which the sample is irradiated;
  a multilayer film mirror provided in a position between the sample and the X-ray source;
  a slit member provided in a position between the sample and the X-ray source and including a slit that limits a width of the X-rays;
  two-dimensional X-ray detection means for two-dimensionally detecting X-rays having exited out of the sample; and
  sample moving means for achieving stepwise movement of the sample relative to the X-rays with which the sample is irradiated to sequentially move the sample to a plurality of step positions, wherein:
  the X-ray source produces the X-rays from a minute focal spot,
  the multilayer film mirror converts the X-rays emitted from the X-ray source into monochromatic, collimated, high-intensity X-rays,
  the direction in which the multilayer film mirror collimates the X-rays coincides with a width direction of the slit of the slit member,
  the step size by which the sample moving means moves the sample is smaller than a width of the slit, and
  the combination of the size of the minute focal spot, the width of the slit, and the intensity of the X-rays that exit out of the multilayer film mirror allows the contrast of an X-ray image produced when the two-dimensional X-ray detection means receives the X-rays for a predetermined period of 1 minute or shorter to be high enough for observation of the X-ray image.

2. The X-ray topography apparatus according to claim 1, further comprising a processor, wherein the processor is configured to:
  acquire a two-dimensional cross-sectional image associated with each of the plurality of step positions, wherein the two-dimensional cross-sectional image is produced by irradiating the sample with the X-rays in each of the plurality of step positions for the predetermined period and detecting X-rays having exited out of the sample irradiated with the X-rays with the two-dimensional X-ray detection means, thereby acquiring a plurality of two-dimensional cross-sectional images,
  form a three-dimensional image by arranging the plurality of two-dimensional cross-sectional images, and
  acquire a second two-dimensional image by extracting data along a flat plane different from measurement planes associated with the three-dimensional image.

3. The X-ray topography apparatus according to claim 2, wherein the processor is further configured to calculate dislocation density based on the second two-dimensional image.

4. The X-ray topography apparatus according to claim 3, wherein the minute focal spot comprises a focal spot so sized as to fall within a circle having a diameter of 100 μm, and the width of the slit ranges from 10 to 50 μm.

5. The X-ray topography apparatus according to claim 4, wherein the multilayer film mirror comprises a parabolic form, so as to allow X-rays incident on the sample to be diffracted in parallel to each other.

6. The X-ray topography apparatus according to claim 5, wherein interplanar spacing of lattice planes in the multilayer film mirror is so differentiated from each other location-to-location that the X-rays incident at different angles of incidence are reflected off the entire surface of the multilayer film mirror.

* * * * *